United States Patent [19]

Ramirez et al.

[11] Patent Number: 5,632,996
[45] Date of Patent: May 27, 1997

[54] BENZOYL PEROXIDE AND BENZOATE ESTER CONTAINING COMPOSITIONS SUITABLE FOR CONTACT WITH SKIN

[75] Inventors: Jose E. Ramirez, Trumbull; Mohan Vishnupad, Monroe, both of Conn.

[73] Assignee: Imaginative Research Associates, Inc., Milford, Conn.

[21] Appl. No.: 422,428

[22] Filed: Apr. 14, 1995

[51] Int. Cl.$^6$ ............................................. A61K 7/48
[52] U.S. Cl. ........................... 424/401; 424/69; 514/846; 514/847; 514/859; 510/131
[58] Field of Search ................ 424/401, 69; 252/90; 514/846, 847, 859

[56] References Cited

U.S. PATENT DOCUMENTS

| | | | |
|---|---|---|---|
| 3,462,370 | 8/1969 | Winter et al. | |
| 3,996,149 | 12/1976 | Burke | 252/160 |
| 4,275,222 | 6/1981 | Scala, Jr. | 560/103 |
| 4,278,655 | 7/1981 | Elmi | 424/47 |
| 4,293,544 | 10/1981 | Elmi | 424/60 |
| 4,322,545 | 3/1982 | Scala, Jr. | 560/103 |
| 4,323,694 | 4/1982 | Scala, Jr. | 560/103 |
| 4,350,681 | 9/1982 | Fulton | 424/53 |
| 4,857,302 | 8/1989 | Decker, Jr. et al. | 424/47 |
| 4,923,900 | 5/1990 | De Villez | 514/714 |
| 4,925,666 | 5/1990 | Decker et al. | 424/401 |
| 5,254,334 | 10/1993 | Ramirez et al. | |
| 5,334,326 | 8/1994 | Bostick | 252/186.26 |

FOREIGN PATENT DOCUMENTS

| | | |
|---|---|---|
| 0038988A1 | 11/1981 | European Pat. Off. |
| 94/13353 | 6/1994 | WIPO . |

OTHER PUBLICATIONS

Scott et al., *Chemical Abstracts*, vol. 104, 1985, #10619.

Tomlinson, *Chemical Abstracts*, vol. 113, 1990, #12122.

Unilever, Derwent Abstract of CA 981695, 1976.

Technical Data Sheet FINSOLV™ TN, Finetex, Inc.

Product (Mar. 1994) Guide Organic Peroxide Products, The Norac Company, Inc.

Product Bulletin Benox®C–35, The Norac Company, Inc.

Product Bulletin (Jul. 1994) Benox®A–70, A–75, A–80, The Norac Company, Inc.

Product Bulletin (Jul. 1994) Benox®B–50, B–55, The Norac Company, Inc.

Product Bulletin (Jul. 1994) Benox®L–40LV, The Norac Company, Inc.

Material Safety Data Sheet Lucidol–75 (Revised May 16, 1994), Elf Atochem North America Inc.

Material Safety Data Sheet Lucidol–98 (Revised May 28, 1992), Elf Atochem North America Inc.

Product Bulletin Organic Peroxides –Lucidol 75–Benzoyl Peroxide with 25% water (Feb. 1994) Elf Atochem North America Inc.

*Primary Examiner*—Thurman K. Page
*Assistant Examiner*—D. Faulkner
*Attorney, Agent, or Firm*—Dilworth & Barrese

[57] ABSTRACT

Non-irritating compositions containing benzoyl peroxide and a non-irritating benzoic acid ester are useful in preparing products suitable for use in contact with the skin.

25 Claims, No Drawings

BENZOYL PEROXIDE AND BENZOATE ESTER CONTAINING COMPOSITIONS SUITABLE FOR CONTACT WITH SKIN

TECHNICAL FIELD

This disclosure relates generally to compositions containing benzoyl peroxide and a benzoic acid ester, which compositions are non-irritating and hence suitable for contact with human skin or tissue. This disclosure also relates to cosmetic, pharmaceutical or cleansing products made with such compositions. More specifically, compositions containing benzoyl peroxide and a non-irritating benzoic acid ester, such as, for example, $C_{12}$–$C_{15}$ alkyl benzoate, and products made therefrom are described herein.

BACKGROUND

Benzoyl peroxide is a non-toxic, colorless, odorless and tasteless crystalline solid with a molecular weight of 242.22 and a melting point of between about 103° to 106° C. Pure (98% active) benzoyl peroxide crystals are commercially available and are extremely flammable and shock sensitive. Accordingly, pure benzoyl peroxide crystals are not normally used in the preparation of cosmetic or pharmaceutical products. Benzoyl peroxide is also commercially available as a 75% crystalline solid with 25% water. These wet, crystalline solids are less flammable and less shock sensitive than the pure, dry crystals and therefore allow safe shipping of the otherwise flammable crystals.

The crystalline powder is gritty and extremely hard and requires milling for several hours in water through high shear mills to prepare a paste having benzoyl peroxide crystals that are sufficiently fine to be of acceptable texture for preparing products for topical use. The aqueous paste prepared from this tedious, expensive and time consuming process can then be used to prepare cosmetic emulsions, containing fine particles of benzoyl peroxide in suspension to form creams, lotions or gels. The milling process must be carried out at low temperature to maintain the stability of the benzoyl peroxide, which starts decomposing at temperatures over 40° C.

Although benzoyl peroxide is soluble in some industrial solvents, such as aromatic solvents, including toluene, methyl-ethyl ketone and benzene, these industrial solvents are highly flammable and are generally too irritating for human use. Therefore preparations containing these industrial solvents are unusable in the over-the-counter or prescription drug preparations. Although acetone is used to a limited degree in some topical foundations, the use of acetone is greatly limited by the fact that acetone is extremely drying to skin and is flammable.

It would be desirable to provide benzoyl peroxide compositions which can be easily and economically prepared, which have a smooth texture appropriate for cosmetic products, and which are non-irritating when placed into contact with skin or other tissue.

SUMMARY

It has now been found that benzoyl peroxide crystalline material can be solubilized in non-irritating benzoic acid esters to provide a composition suitable for preparing cosmetic or pharmaceutical products. The preferred benzoic acid esters, $C_{12}$–$C_{15}$ alkylbenzoates, are a non-toxic, non-irritating, non-sensitizing and non-comedogenic, water insoluble, readily emulsifiable esters. By using such esters, compositions in accordance with this disclosure can be safely placed into contact with human skin or other tissue without causing significant irritation.

The crystalline nature of benzoyl peroxide is transformed into a soft, fine amorphous benzoyl peroxide by simply mixing with the non-irritating benzoic acid ester at room temperature conditions. Advantageously, no extensive shear mixing or heat is required to produce a smooth, soft, non-crystalline mixture of benzoyl peroxide with the benzoic acid ester. Because there is no heat involved in this process, benzoyl peroxide (which is extremely sensitive to heat and starts to decompose over 40° C.) is completely stable in the ester. Due to this increased stability and the non-irritating nature of the ester, the present compositions provide an excellent vehicle for use in cosmetic lotions, gels and creams and in drug preparations.

The present compositions contain non-crystalline, fine benzoyl peroxide and are either a dispersion or a paste depending on the concentration of benzoyl peroxide that is combined with the ester. While emulsions are embraced by this disclosure, it should be understood that the benzoyl peroxide/ester mixture is water insoluble. Anhydrous benzoyl peroxide compositions in accordance with this disclosure provide a long shelf life, remaining stable even at higher temperature and are particularly preferred.

DETAILED DESCRIPTION OF PREFERRED EMBODIMENTS

Non-irritating benzoyl peroxide compositions in accordance with this disclosure include a non-irritating benzoic ester mixed with benzoyl peroxide. Long chain alkylbenzoates are one type of benzoic acid ester useful in forming the present compositions. The alkyl group of the alkyl benzoate preferably contains from 12 to 15 carbon atoms. Suitable alkyl benzoates are commercially available, for example, under the tradename FINSOLV from Finetex, Inc., Elmwood Park, N.J. FINSOLV-TN is particularly preferred for use in cosmetic preparations. In another embodiment, FINSOLV-P (PPG-15 stearyl ether benzoate) is used as the benzoate ester in the preparation of compositions useful as cleansing products. Other suitable benzoate esters include Poloxamer 182 Dibenzoate, Poloxamer 105 benzoate and stearyl benzoate. Suitable benzoic acid esters are described for example in U.S. Pat. Nos. 4,275,222; 4,278,655; 4,293,544; 4,322,545; and 4,323,694 the disclosures of which are incorporated herein be reference.

In preparing compositions in accordance with this disclosure, benzoyl peroxide is simply mixed with the benzoic acid ester, preferably at room temperature. As previously mentioned, benzoyl peroxide is normally commercially available as either pure (98% active) crystals or in a wet crystalline state containing 70 to 80% active benzoyl peroxide in 20–30% water. Such benzoyl peroxide products are available from The Norac Company Inc., Azusa, Calif. under the BENOX tradenames or from Elf Atochem North America, Inc., Philadelphia, Pa. under the LUCIDOL tradenames. Any of these or other forms of benzoyl peroxide can be mixed with a benzoic acid ester to form compositions in accordance with this disclosure.

The amount of benzoyl peroxide mixed with the benzoic acid ester will vary depending on a number of factors, including, for example, the activity of benzoyl peroxide, the ultimate form of the product and the particular benzoic acid ester employed. Generally, the benzoyl peroxide will constitute from 1 to 99 weight percent of the benzoyl peroxide/benzoate ester mixture. Preferably, the benzoyl peroxide constitutes from about 3.75 to about 70 weight percent of the benzoyl peroxide/ester mixture. Most preferably, the benzoyl peroxide constitutes from about 30 to about 60 weight percent of the benzoyl peroxide/ester mixture.

The manufacturing process for making the present compositions is much simpler, safer and more economical than prior art techniques since benzoyl peroxide can be added to the ester form a mixture at low temperatures, e.g., in the range of 25°–27° C. Additionally, the benzoyl peroxide/ester mixture also can be added to other ingredients to form desired products, e.g., emulsions, lotions, creams or gels at low temperatures. In these processes, since benzoyl peroxide is never in contact with substantial heat, the possibility of decomposition or fire is greatly reduced.

Furthermore, the higher affinity of benzoyl peroxide to $C_{12}$–$C_{15}$ alkylbenzoate offers a unique method for preparing anhydrous benzoyl peroxide without subjecting the composition to any heat during processing. For example, when benzoyl peroxide-wet crystals containing 25% water are mixed with $C_{12}$–$C_{15}$ alkylbenzoate, the benzoate ester (which has a stronger affinity for benzoyl peroxide than water) totally replaces water in the process of changing the crystalline benzoyl peroxide to a fine soft benzoyl peroxide slurry. This composition can then be filtered to remove substantially all the water from the composition thereby providing a fine textured, substantially, anhydrous benzoyl peroxide paste composition.

Additionally, the soft, anhydrous benzoyl peroxide/$C_{12}$–$C_{15}$ alkylbenzoate paste can then be washed with anhydrous 200 proof alcohol or any suitable solvent which dissolves the ester leaving a fine, amorphous 100% pure benzoyl peroxide as a residue. Thus, a novel process for purification of benzoyl peroxide has also been discovered. This fine, amorphous powder can be used in cosmetic preparations or plastic industry or as an aid to polymerization much more effectively than the pure (98% active) crystalline, hard, granular benzoyl peroxide which is currently commercially available.

To show that benzoyl peroxide mixed with $C_{12}$–$C_{15}$ alkylbenzoate ester does not go through any chemical structural changes, analytical (gas chromatograph) tests were conducted on the neat benzoyl peroxide (98% active sample (LUCIDOL-98) as received from Elf Atochem) and on a 10% benzoyl peroxide dispersion in $C_{12}$–$C_{15}$ alkylbenzoate. The activity of benzoyl peroxide in the $C_{12}$–$C_{15}$ alkylbenzoate is essentially the same as in the commercially obtained pure crystals, showing that the benzoyl peroxide remains intact, without any chemical changes, when mixed with the benzoate ester.

The following formulations are representative of mixtures useful in purifying benzoyl peroxide or in preparing products for application to the skin.

| Formulation | 1 | 2 | 3 | 4 | 5 | 6 | 7 |
|---|---|---|---|---|---|---|---|
| LUCIDOL-98 (BP 98%) | 5.00 | 10 | 30 | 40 | 50 | 60 | 70 |
| FINSOLV TN $C_{12}$–$C_{15}$ Alkylbenzoate | 95.00 | 90 | 70 | 60 | 50 | 40 | 30 |

| Formulation | 8 | 9 |
|---|---|---|
| LUCIDOL-75 (BP 75%, Water 25%) | 5.00 | 10 |
| FINSOLV TN ($C_{12}$–$C_{15}$ Alkylbenzoate) | 95.00 | 90 |

The formulations containing higher concentrations of benzoyl peroxide in the ester are very useful in cosmetic formulations, wherein 5% and 10% benzoyl peroxide can be derived from the benzoyl peroxide/ester concentrate paste.

By mixing benzoyl peroxide and $C_{12}$–$C_{15}$ alkyl benzoate at room temperature, the ester will plasticize the benzoyl peroxide, replacing all the bound water which can be filtered off. The anhydrous non-crystalline benzoyl peroxide slurry is washed thoroughly with 200 proof alcohol or any volatile solvent which dissolves the ester and any fillers out, leaving anhydrous amorphous purified benzoyl peroxide residue.

The following anhydrous benzoyl peroxide suspension formulations are suitable for use as formulated or further combined with other ingredients.

|  |  | % |
|---|---|---|
| I. | Benzoyl Peroxide 98% | 10.0 |
|  | $C_{12}$–$C_{15}$ Alkylbenzoate | 20.0 |
|  | Volatile Silicone | 10.00 |
|  | Anhydrous Alcohol (200) | 80.00 |
| II. | Benzoyl Peroxide 75% | 10.00 |
|  | $C_{12}$–$C_{15}$ Alkylbenzoate | 20.00 |
|  | Volatile Silicone | 10.00 |
|  | Anhydrous Alcohol (200 Proof) | 60.00 |

In the second formulation, a small amount of residual water (up to 3%) is functional. Any more than 5% water will precipitate the benzoyl peroxide and make the composition unsuitable for skin care applications. Thus, it is contemplated that compositions containing less than 5% water are anhydrous for purposes of the compositions described herein. These anhydrous benzoyl peroxide suspensions can be used directly as a skin clarifying liquid for ache skin.

An anhydrous benzoyl peroxide cream can be prepared having the following formulation:

|  | % |
|---|---|
| Petrolatum | 6.5 |
| Polyethylene | 2.0 |
| Silicone-copolyol | 30.0 |
| Silica | 2.0 |
| Dry-Flo Starch | 39.0 |
| Bentonite Clay | 1.0 |
| Zinc Lactate | 0.5 |
| Glycolic Acid | 2.0 |
| Benzoyl Peroxide | 10.0 |
| $C_{12-15}$ Alkyl Benzoate | 7.0 |

To prepare the anhydrous cream, the petrolatum, polyethylene and silicone-copolyol are heated to 80° C. to form an oil phase. The silica, starch, clay, zinc lactate and glycolic acid are pre-milled to form a fine powder. The powder is thoroughly mixed with the oil phase while maintaining the temperature at 80° C. Mixing is continued until a smooth, non-gritty paste is produced. The paste is cooled to 27°–30° C. A mixture of benzoyl peroxide and $C_{12-15}$ alkyl benzoate is prepared at room temperature and mixed well with cooled paste until a uniform anhydrous cream is produced.

The following formulation is suitable for use as a lotion for treatment of acne.

| Acne Lotion With | % |
|---|---|
| Water | 62.9 |
| Steareth - 20 | 0.6 |
| glycerin | 6.0 |
| Benzoyl Peroxide | 10 |
| $C_{12}$–$C_{15}$ Alkylbenzoate | 5 |

-continued

| Acne Lotion With | % |
| --- | --- |
| Petrolatum | 5.0 |
| DryFlo Starch | 3.0 |
| Dimethicone | 1.0 |
| $Na_2$-EDTA | 0.10 |
| Cetearyl Alcohol | 4.50 |
| Steareth - 2 | 1.30 |
| Titanium Dioxide | 0.30 |
| Fragrance | 0.30 |

To prepare the foregoing lotion, the water steareth-20, glycerine and $Na_2$-EDTA are mixed to form a water phase. The petrolatum, starch, dimethicone, cetearyl alcohol, steareth-2 and $TiO_2$ are mixed to form an oil phase. The water and oil phases are both heated to 70° C., combined combined and mixed thoroughly until a smooth emulsion is produced. The emulsion is then cooled to 27° C. A paste of benzoyl peroxide in $C_{12}$–$C_{15}$ alkylbenzoate is prepared at room temperature and added to the emulsion with mixing. Mixing is continued until a smooth lotion/cream is produced. Fragrance is then added.

Such acne preparations can thus be prepared without any high shear milling equipment to grind the benzoyl peroxide crystals. Additionally, benzoyl peroxide is not subject to heat during the preparation process. Therefore, such benzoyl peroxide preparations are more stable and will have long shelf life.

The benzoyl peroxide/benzoic acid ester paste prepared by cold mixing can be used for any kind of ache preparation such as lotion, cream or gel. Also the benzoyl peroxide/ benzoic acid ester paste can be added to soap bars or syndet cleansing bars, without subjecting the benzoyl peroxide to any heat or high shear mixing. The soaps and syndet bar prepared by using a paste of benzoyl peroxide/benzoic acid ester will be more stable and will have better shelf life.

The following formulations exemplify soap and syndet bars in accordance with this disclosure:

|  | % |
| --- | --- |
| Soap Bar |  |
| Sodium Tallowate | 64.0 |
| Sodium Cocoate | 16.0 |
| Benzoyl Peroxide | 10.0 |
| $C_{12-15}$ Alkyl Benzoate | 5.0 |
| Coconut Acid | 4.0 |
| Fragrance | 0.25 |
| Titanium Dioxide | 0.2S |
| BHT | 0.25 |
| Disodium-EDTA | 0.25 |
| Syndet Cleansing Bar |  |
| Sodium Cocoyl Isethionate | 45.0 |
| Stearic Acid | 16.0 |
| Benzoyl Peroxide | 10.0 |
| Sodium Isethionate | 8.0 |
| $C_{12-15}$ Alkyl Benzoate | 5.0 |
| Sodium Cocoate | 5.0 |
| Sodium Stearate | 5.0 |
| Water | 4.5 |
| Fragrance | 0.4 |
| Sodium Chloride | 0.4 |
| Titanium Dioxide | 0.35 |
| $Na_2$-EDTA | 0.35 |

The benzoyl peroxide/benzoic acid ester mixture can be combined with one or more cleansing agent. The cleansing agent may be selected from soaps or synthetic surfactants. Combinations of soaps and synthetic surfactants may be employed. Any combination of known synthetic surfactants may be employed. Those skilled in the art will be able to envision combinations of known surfactants capable of providing desired characteristics, e.g., degree of foaming and physical characteristics. The cleansing composition can be in the form of a liquid, cream, gel or bar. The following formulation is an example of a benzoyl peroxide foaming cleansing cream in accordance with this disclosure:

| Ingredient | % |
| --- | --- |
| Petrolatum | 17.6 |
| Sodium Cocoylisethionate | 5.0 |
| Alpha-olefin sulfonate | 2.0 |
| Titanium dioxide | 0.3 |
| Glycerine | 60.0 |
| Benzoyl Peroxide | 10.0 |
| $C_{12-15}$ Alkyl Benzoate | 5.0 |
| Fragrance | 0.1 |

To prepare the foaming cleansing cream, the petrolatum is heated to 80° C. and the isethionate, sulfonate and titanium dioxide are added. The mixture is milled until a smooth paste is obtained. The glycerine is added at 80° C. to the oil phase with high shear mixing to produce a smooth, creamy paste. The paste is cooled to 27°–30° C. A benzoyl peroxide/$C_{12-15}$ alkyl benzoate mixture is prepared at room temperature and added to the detergent paste. Mixing is continued until a uniform creamy paste is produced. Notably, no milling or heat is required while adding the benzoyl peroxide/ester paste, thereby increasing the shelf life of the benzoyl peroxide preparation.

It is also contemplated that dry powder benzoyl peroxide-containing compositions can be prepared in accordance with this disclosure. An example of such a dry powder formulation is given below:

| Dry Powder Formulation | % |
| --- | --- |
| Benzoyl Peroxide | 10.0 |
| $C_{12-15}$ AlkylBenzoate Ester | 7.0 |
| Talc | 51.8 |
| Corn Starch | 30.0 |
| $TiO_2$ | 0.5 |
| Iron Oxide | 0.2 |
| Silica | 0.5 |

By utilizing the unique properties of benzoate ester in combination with benzoyl peroxide, it is possible to blend a benzoyl peroxide/ester paste prepared as described above with other dry ingredients to form a powder mixture useful, for example, as a facial powder, with or without skin tone pigment. Since there is no heat involved in the preparation process, the anhydrous powder provides an excellent facial compact powder, especially for ache skin.

It will be understood that various modifications may be made to the embodiments disclosed herein. For example, a variety of optional components such as, for example, humectants, emollients, dyes, medicaments, texture modifiers, fillers and/or emulsifiers can be combined with the benzoyl peroxide/benzoic acid ester mixtures described herein to formulate acceptable non-irritating products for topical use. Therefore, the above description should not be construed as limiting, but merely as exemplifications of preferred embodiments. Those skilled in art will envision other modifications within the scope and spirit of the claims appended hereto.

What is claimed is:

1. A composition for contact with skin comprising:

benzoyl peroxide; and a mixture of non-irritating long chain alkyl benzoates, the composition being substantially anhydrous.

2. A composition as in claim 1, wherein the mixture of non-irritating long chain alkyl benzoates is $C_{12}$–$C_{15}$ alkyl benzoate.

3. A composition as in claim 1, wherein benzoyl peroxide comprises from about 0.1 to about 25 weight percent of the composition.

4. A cleansing composition comprising:

benzoyl peroxide;

a mixture of non-irritating long chain alkyl benzoates; and a cleansing agent selected from the group consisting of soap and synthetic detergents.

5. A cleansing composition as in claim 4 wherein the mixture of non-irritating long chain alkyl benzoates is $C_{12}$–$C_{15}$ alkyl benzoate.

6. A cleansing composition as in claim 4, wherein the cleansing agent is a synthetic detergent.

7. A cleansing composition as in claim 4, which is substantially anhydrous.

8. A composition as in claim 4 in the form of a bar.

9. A method of preparing a cleansing composition comprising mixing benzoyl peroxide with a combination of non-irritating long chain alkyl benzoate esters to provide a mixture; and combining the mixture with at least one cleansing agent selected from the group consisting of soaps and synthetic detergents.

10. A method as in claim 9 wherein, the mixing step comprises mixing benzoyl peroxide with a $C_{12}$–$C_{15}$ alkyl benzoate mixture.

11. A method as in claim 9, wherein the mixing step comprises mixing benzoyl peroxide in combination with water with a combination of non-irritating long chain alkyl benzoate esters.

12. A method as in claim 9, wherein the mixture is combined with at least one synthetic detergent.

13. A method as in claim 9, further comprising the step of removing water from the mixture prior to the combining step.

14. A method as in claim 9, wherein the mixing step is conducted at substantially room temperature.

15. A method as in claim 14, wherein the combining step is conducted at substantially room temperature.

16. A method as in claim 9, further comprising the step of forming a bar from the composition.

17. A method as in claim 15, further comprising the step of forming a bar from the composition.

18. A method of treating acne comprising preparing a composition containing benzoyl peroxide and a mixture of non-irritating long chain alkyl benzoates; and contacting the composition with the skin of a person afflicted with acne.

19. A method as in claim 18, wherein the step of preparing a composition comprises mixing benzoyl peroxide with a $C_{12}$–$C_{15}$ alkyl benzoate mixture.

20. A method as in claim 18, wherein the step of preparing a composition comprises mixing a water-containing benzoyl peroxide component with a non-irritating benzoic acid ester.

21. A method as in claim 20, wherein the step of preparing a composition further comprises the step of removing water, whereby a substantially anhydrous composition is prepared.

22. A method as in claim 18, wherein the step of preparing a composition comprises forming mixing benzoyl peroxide with a non-irritating benzoic acid ester to form a mixture, and combining the mixture with at least one cleansing agent.

23. A method for obtaining purified benzoyl peroxide comprising:

mixing wet benzoyl peroxide crystal with a benzoic acid ester;

filtering off water to provide a substantially anhydrous mixture of benzoyl peroxide and benzoic acid ester;

contacting the substantially anhydrous mixture with a solvent to dissolve the benzoic ester; and removing the solvent to recover substantially pure solid benzoyl peroxide.

24. A method as in claim 23, wherein the benzoic ester is $C_{12}$–$C_{15}$ alkyl benzoate.

25. A method as in claim 23 wherein the solvent is an alcohol.

* * * * *